(12) United States Patent
Setiawan et al.

(10) Patent No.: US 9,078,810 B2
(45) Date of Patent: *Jul. 14, 2015

(54) TRANSDERMAL DELIVERY SYSTEM

(71) Applicant: Acrux DDS Pty Ltd., West Melbourne, Victoria (AU)

(72) Inventors: Kerrie Setiawan, West Melbourne (AU); Adam Watkinson, Melbourne (AU)

(73) Assignee: ACRUX DDS PTY LTD, West Melbourne, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/887,758

(22) Filed: May 6, 2013

(65) Prior Publication Data

US 2013/0317122 A1    Nov. 28, 2013

Related U.S. Application Data

(63) Continuation of application No. 12/740,663, filed as application No. PCT/AU2008/001614 on Oct. 13, 2008, now abandoned.

(60) Provisional application No. 60/984,787, filed on Nov. 2, 2007.

(51) Int. Cl.
| | |
|---|---|
| *A61K 9/00* | (2006.01) |
| *A61K 9/12* | (2006.01) |
| *A61K 31/56* | (2006.01) |
| *A61K 31/57* | (2006.01) |
| *A61K 47/10* | (2006.01) |
| *A61K 31/565* | (2006.01) |

(Continued)

(52) U.S. Cl.
CPC ............. *A61K 9/0014* (2013.01); *A61K 9/12* (2013.01); *A61K 31/56* (2013.01); *A61K 31/565* (2013.01); *A61K 31/568* (2013.01); *A61K 31/57* (2013.01); *A61K 31/573* (2013.01); *A61K 47/10* (2013.01); *A61M 35/003* (2013.01); *A61K 47/14* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 6,299,900 | B1 | 10/2001 | Reed et al. |
| 6,818,226 | B2 | 11/2004 | Reed et al. |

(Continued)

FOREIGN PATENT DOCUMENTS

| | | |
|---|---|---|
| EP | 0 328 806 A2 | 8/1989 |
| EP | 0 409 383 A2 | 1/1991 |

(Continued)

OTHER PUBLICATIONS

Campbell, I. M. Introduction to Synthetic Polymers, Oxford Science Publications: 1994, 99. 18-20.*

(Continued)

*Primary Examiner* — Mina Haghighatian
*Assistant Examiner* — Erin Hirt
(74) *Attorney, Agent, or Firm* — Foley & Lardner LLP

(57) ABSTRACT

A transdermal delivery system comprising a composition comprising a physiologically active agent and a penetration enhancer wherein the penetration enhancer comprises a combination of (i) an ester of salicylic acid, preferably selected from the $C_6$ to $C_{30}$ aliphatic ester of salicylic acid and (ii) polyethylene glycol (PEG) of average molecular weight no more than 300.

19 Claims, 10 Drawing Sheets

(51) Int. Cl.
*A61K 31/568* (2006.01)
*A61K 31/573* (2006.01)
*A61M 35/00* (2006.01)
A61K 47/14 (2006.01)
A61K 47/32 (2006.01)

(56) References Cited

U.S. PATENT DOCUMENTS

| | | |
|---|---|---|
| 6,916,486 B2 | 7/2005 | Klose et al. |
| 6,916,487 B2 | 7/2005 | Klose et al. |
| 6,923,983 B2 | 8/2005 | Morgan et al. |
| 6,929,801 B2 | 8/2005 | Klose et al. |
| 6,964,777 B2 | 11/2005 | Klose et al. |
| 6,998,138 B2 | 2/2006 | Chew et al. |
| 7,094,422 B2 | 8/2006 | Chew et al. |
| 7,387,789 B2 | 6/2008 | Klose et al. |
| 7,438,203 B2 | 10/2008 | Reed et al. |
| 8,435,944 B2 * | 5/2013 | Dipietro et al. ............. 514/10.2 |
| 8,466,138 B2 * | 6/2013 | Malladi et al. ............. 514/177 |
| 2002/0103372 A1 * | 8/2002 | Iishi et al. ............. 540/555 |
| 2005/0002868 A1 | 1/2005 | Gonda et al. |
| 2005/0090488 A1 * | 4/2005 | Andrews et al. ............. 514/220 |
| 2005/0175680 A1 | 8/2005 | Morgan et al. |
| 2005/0181032 A1 | 8/2005 | Wilkins et al. |
| 2005/0186141 A1 * | 8/2005 | Gonda et al. ............. 424/45 |
| 2006/0018937 A1 | 1/2006 | Friedman et al. |
| 2006/0275218 A1 * | 12/2006 | Tamarkin et al. ............. 424/45 |
| 2006/0280783 A1 | 12/2006 | Dipietro et al. |
| 2007/0071803 A1 | 3/2007 | Reed et al. |
| 2007/0275943 A1 | 11/2007 | Morgan et al. |
| 2008/0131494 A1 | 6/2008 | Reed et al. |
| 2008/0152597 A1 | 6/2008 | Reed et al. |
| 2010/0279988 A1 | 11/2010 | Setiawan et al. |
| 2010/0297032 A1 | 11/2010 | Setiawan et al. |
| 2010/0322884 A1 * | 12/2010 | DiPietro et al. ............. 424/68 |

FOREIGN PATENT DOCUMENTS

| | | |
|---|---|---|
| EP | 1 586 571 A1 | 10/2005 |
| JP | 1-308225 | 12/1989 |
| WO | WO 93/10201 A1 | 5/1993 |
| WO | WO 94/06452 A1 | 3/1994 |
| WO | WO 94/07478 A1 | 4/1994 |
| WO | WO 00/44347 A1 | 8/2000 |
| WO | WO 00/45795 A2 | 8/2000 |
| WO | WO 03/039597 A1 | 5/2003 |
| WO | WO 2005/049025 A1 | 6/2005 |
| WO | WO 2006/108719 A1 | 10/2006 |
| WO | WO 2007/016766 A1 | 2/2007 |

OTHER PUBLICATIONS

The birth of the 'psychic energizer' accessed on Jun. 16, 2012 at mindhacks.com/2009/10/20/birth-of-the-psychic-energizer/.*
Vippagunta et al. "Crystalline Solids," Advanced Drug Delivery Reviews, 2001, 48, 3-26.*
Braga et al. Chem. Commun., "Making Crystals from Crystals: a green route to crystal engineering and polymorphism," 2005, pp. 3635-3645.*
Seddon, K.R., "Pseudopolymorph: a polemic," Crystal Growth & Design, 2004, 4(6), pp. 1087, web release date Oct. 19, 2004.*
PEG-200 Info sheet, Sigma-Aldrich (http://www.sigmaaldrich.com/catalog/product/fluka/81150?lang=en&region=US) no date available, no page numbers.*
TSAI et al., "Molecular weight dependence of polyethylene glycol penetration across acetone-disrupted permeability barrier," Arch. Dermatol. Res., vol. 293, pp. 302-307, 2001.
U.S. Appl. No. 13/887,719, May 6, 2013, Setiawan et al.
European Search Report issued on Oct. 7, 2010 in application number 08845600.9.
European Search Report issued on Nov. 2, 2010 in application number 08845547.2.
Morgan et al., "Enhanced Skin Permeation of Sex Hormones with Novel Topical Spray Vehicles," *Journal of Pharmaceutical Sciences*, vol. 87, No. 10, pp. 1213-1218, Oct. 1998.
David W. Osbourne et al., "Skin Penetration Enhancers Cited in the Technical Literature", Pharmaceutical Technology, Nov. 1997, pp. 58-66.
Timothy M. Morgan et al., "Transdermal Delivery of Estradiol in Postmenopausal Women with a Novel Topical Aerosol", Journal of Pharmaceutical Sciences, vol. 87, No. 10, Oct. 1998, pp. 1226-1228.
International Search Report PCT/AU2008/001613 dated Jan. 22, 2009.
Office Action issued on May, 17, 2012 in U.S. Appl. No. 12/740,666 (US 2010/0279988).
Office Action issued on Dec. 4, 2012 in U.S. Appl. No. 12/740,666 (US 2010/0279988).
Liaw et al., "The effect of polyethylene glycol molecular weight on corneal transport and the related influence of penetration enhancers," International Journal of Pharmaceutics, vol. 88, pp. 125-140, 1992.
International Search Report PCT/AU2008/001614 dated Jan. 27, 2010.
David W. Osborne et al. "Skin Penetration Enhancers Cited in the Technical Literature", Pharmaceutical Technology, Nov. 1997, pp. 58-66.
Ed: Limmer D. "Remington: The science and practice of pharmacy", $20^{th}$ Ed. Published 2000, Lippincott Williams and Wilkins, ISBN 0-683-306472.
Pankaj Karande et al., "Insights into synergistic interactions in binary mixtures of chemical permeation enhancers for transdermal drug delivery", Journal of Controlled Release 115 (2006) 85-93.
Joseph A. Nicolazzo et al., "Synergistic enhancement of testosterone transdermal delivery", Journal of Controlled Release 103 (2005) 577-282.
H.-Y. Thong et al., "Percutaneous Penetration Enhances: An Overview", Skin Pharmacology and Physiology, 2007:20 273-282.
Campbell, "Average molecular masses and polydisperity", Introduction to Synthetic Polymers, pp. 18-20, 1994.
Mindhacks, "The birth of the 'psychic energizer'," www. Mindhacks.com/2009/10/20/birth-of-psychic-energizer, accessed on Jun. 16, 2012.
Vippagunta et al., "Crystalline Solids," Advanced Drug Delivery Reviews, vol. 48, pp. 3-26, 2001.
Braga et al., "Making crystals from crystals: a green route to crystal engineering and polymorphism," Chem. Commun., pp. 3635-3645, 2005.
Seddon, "Pseudopolymorph: a polemic," Crystal Growth & Design, vol. 4, No. 6, p. 1087, 2004.
Office Action issued on Jun. 19, 2012 in U.S. Appl. No. 12/740,663 (US 2010/0297032).
Office Action issued on Jan. 23, 2013 in U.S. Appl. No. 12/740,663 (US 2010/0297032).
Office Action issued on Apr. 11, 2014 in U.S. Appl. No. 13/887,719 (US 2013/0317462).

* cited by examiner

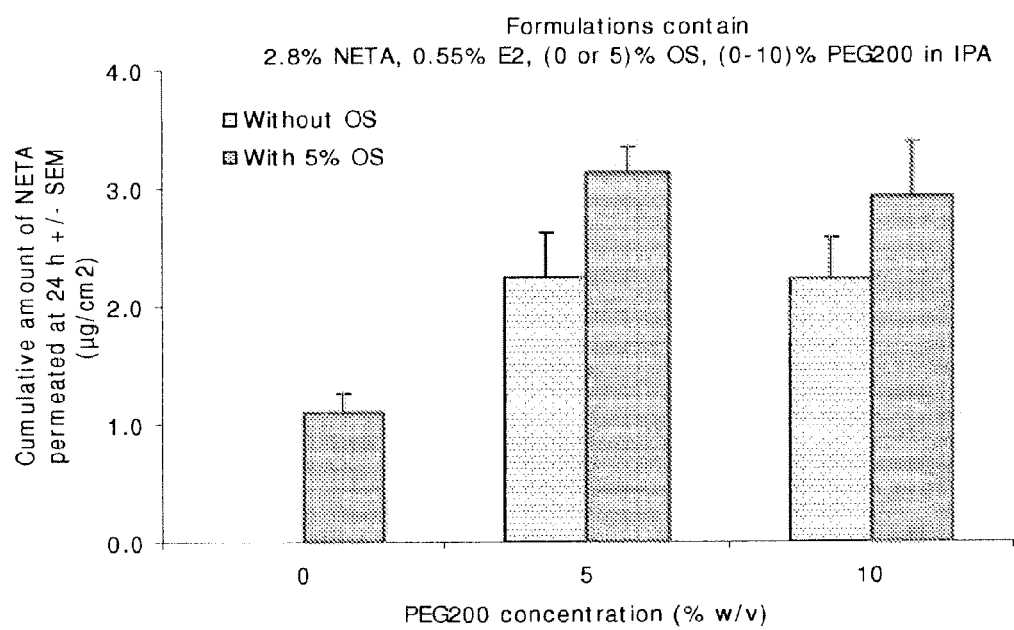
Figure 1: Norethisterone Acetate permeation obtained from the application of Compositions 2-5 compared against application of a control.

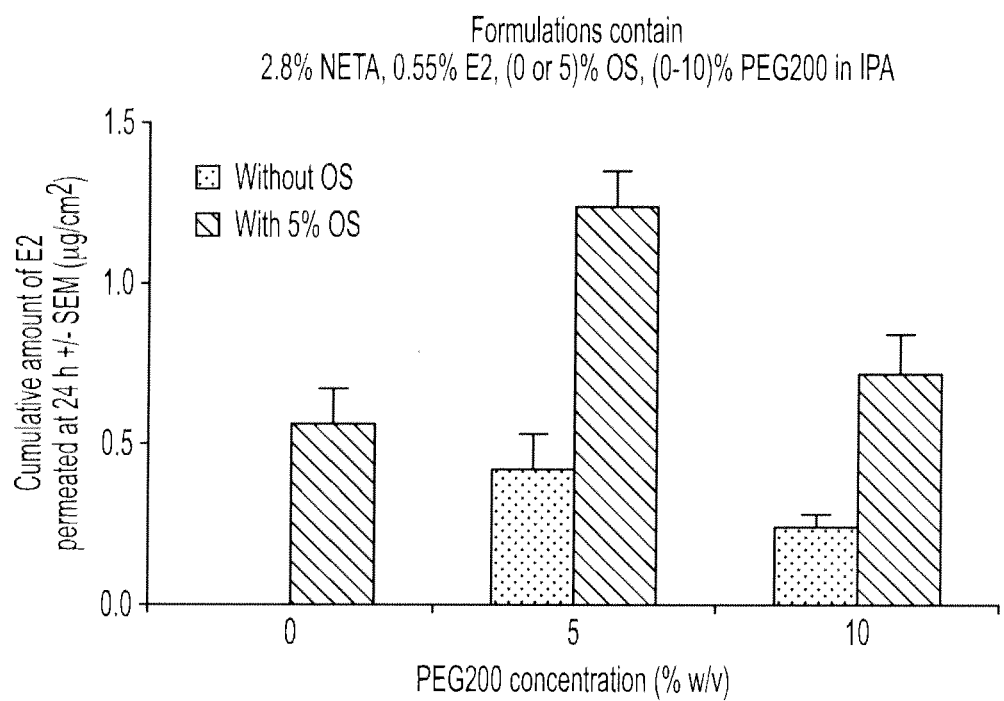
Figure 2: Estradiol permeation obtained from the application of Compositions 2-5 in accordance with the invention compared with application of control Composition 1.

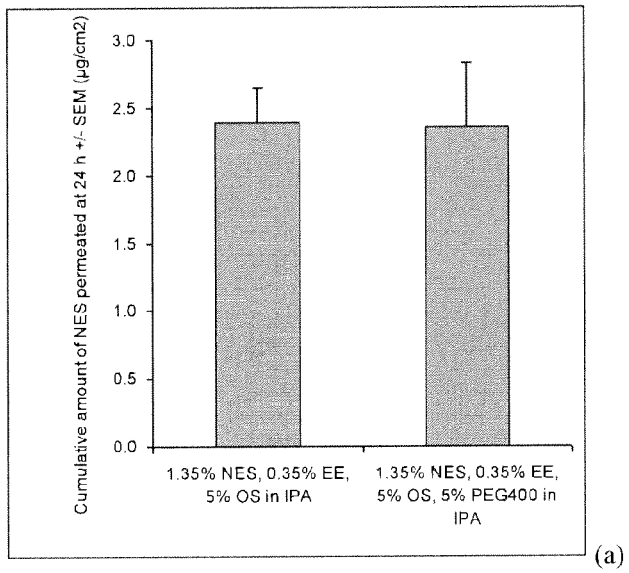
Figure 3a: Nestorone permeation obtained from the application of Composition 2 (not of the invention) compared against application of a control composition 1.
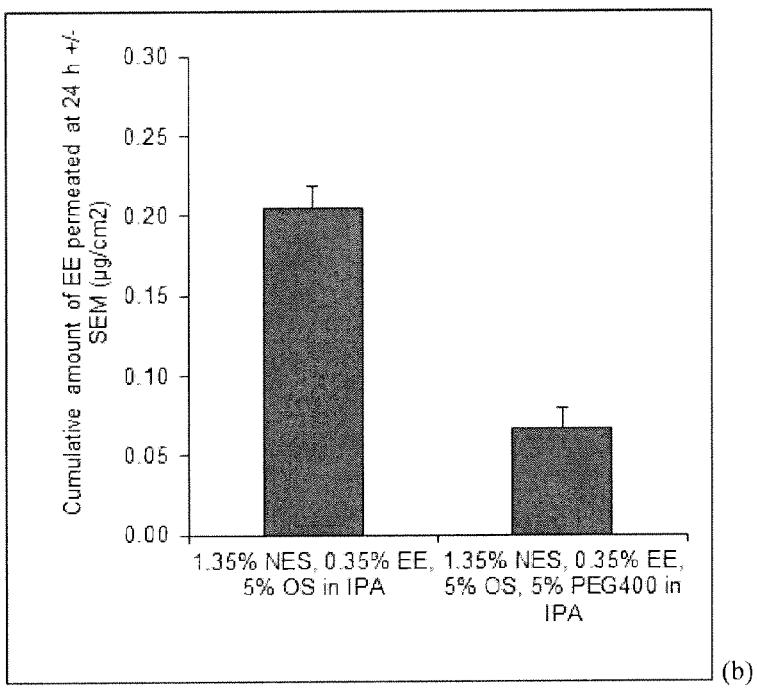
Figure 3b: Ethinylestradiol permeation obtained form the application of Composition 2 (not of the invention) compared against application of a control composition 1.

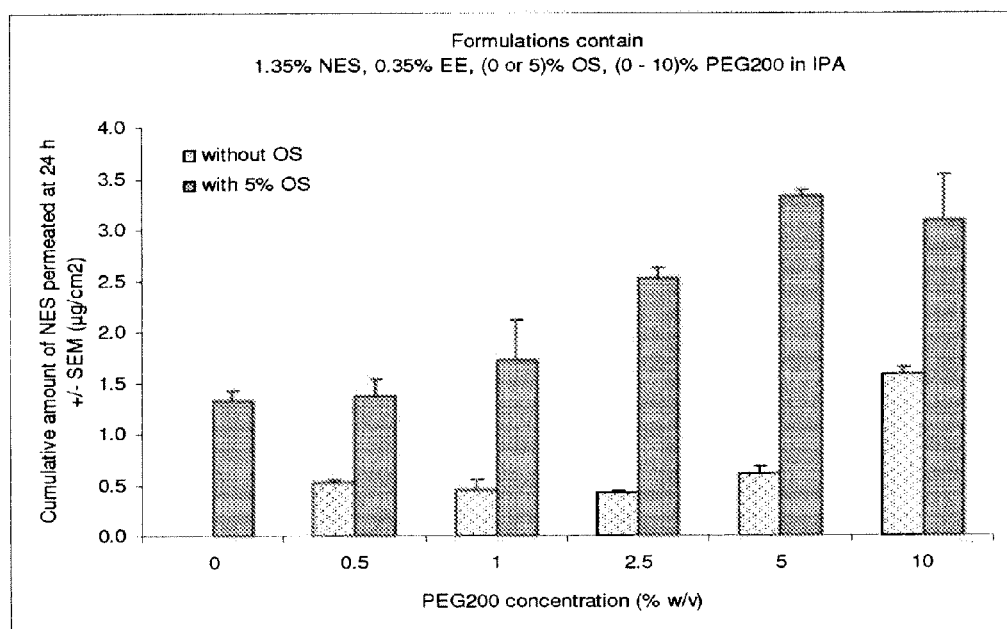
Figure 4: Nestorone permeation obtained from the application of Compositions 3-12 compared against application of the Composition 1 control.

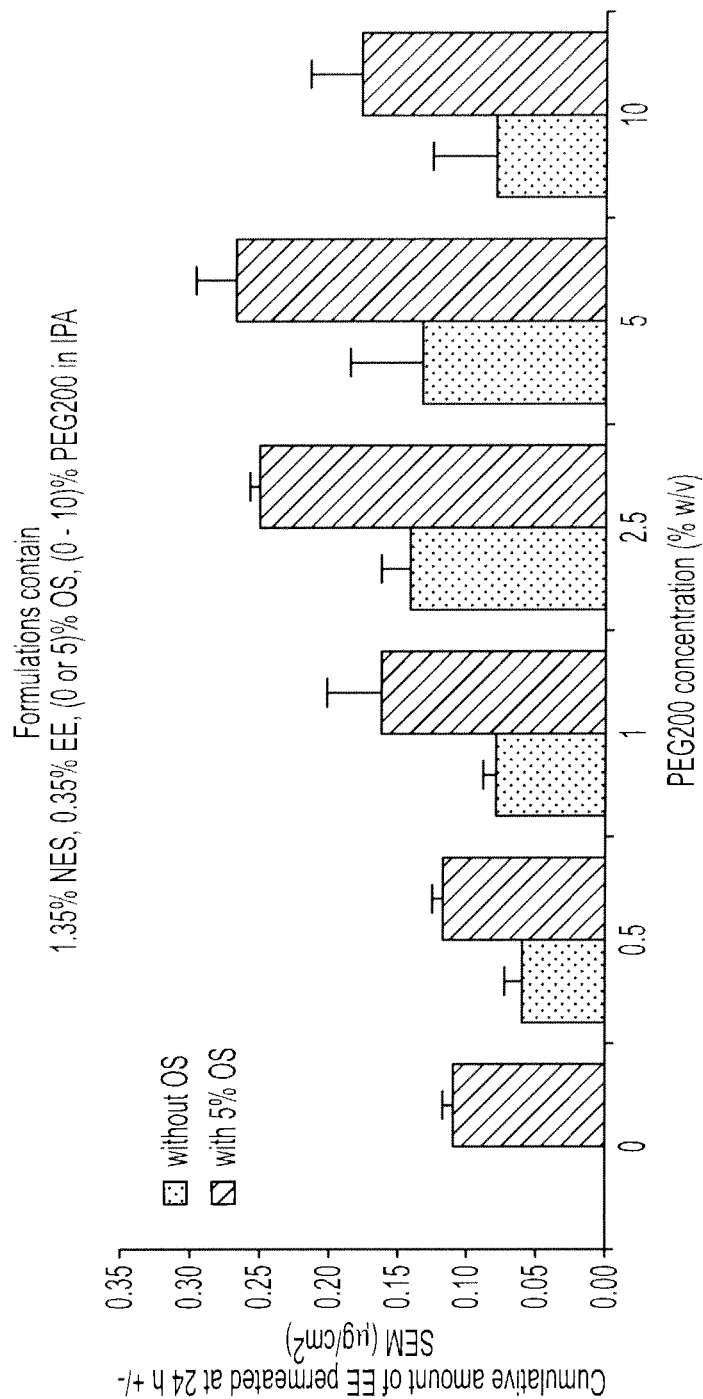
Figure 5: Ethinylestradiol permeation obtained from the application of Compositions 3-12 compared against application of the Composition 1 control.

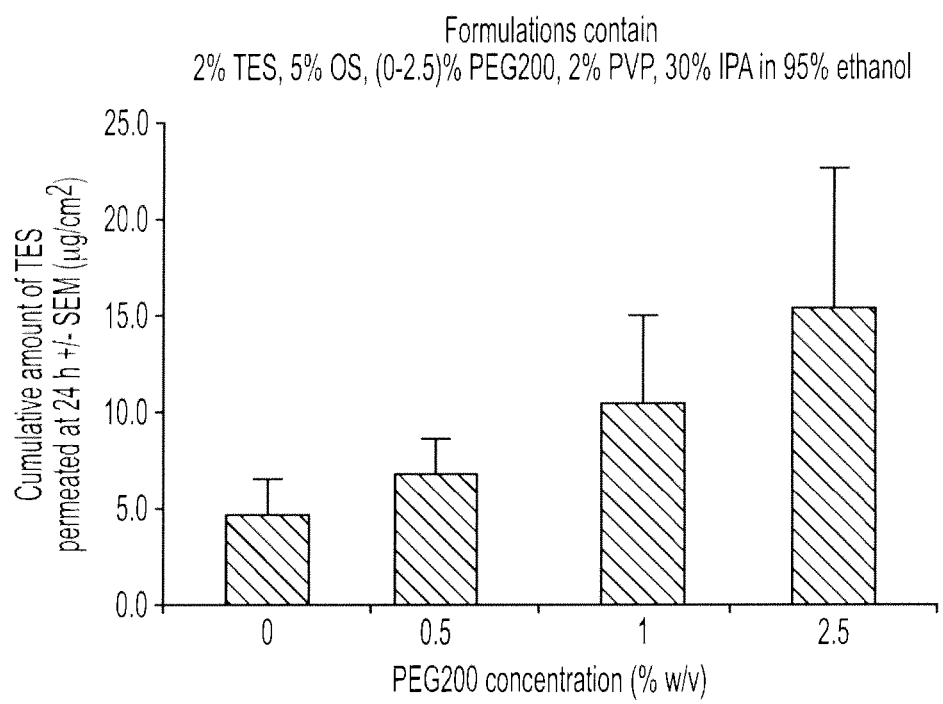
Figure 6 (Comp 1): Testosterone permeation obtained from the application of Compositions 2-4 compared against application of a control.

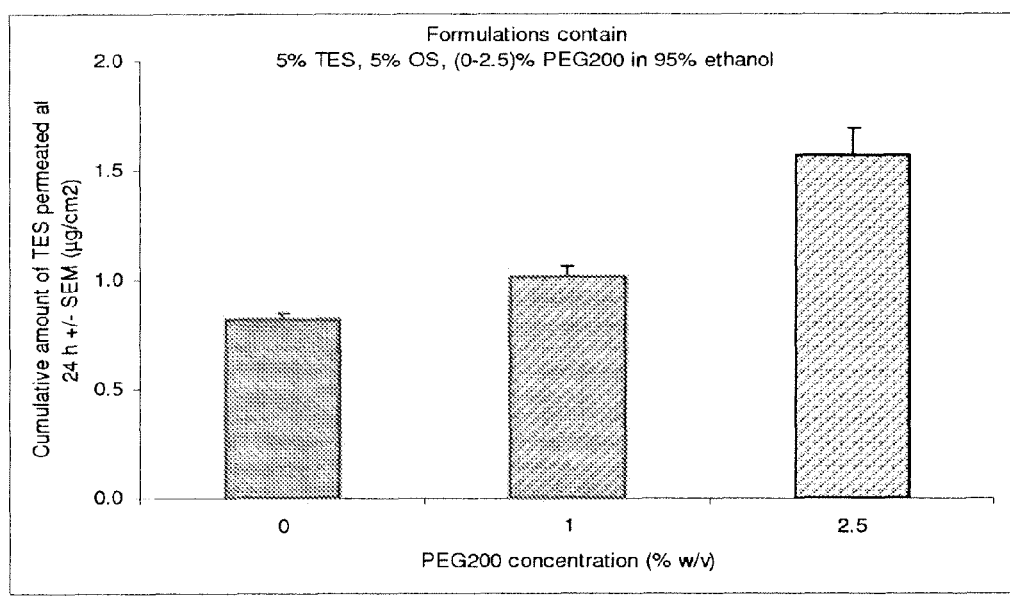
Figure 7: Testosterone permeation obtained from the application of Compositions 2-3 compared against application of a control.

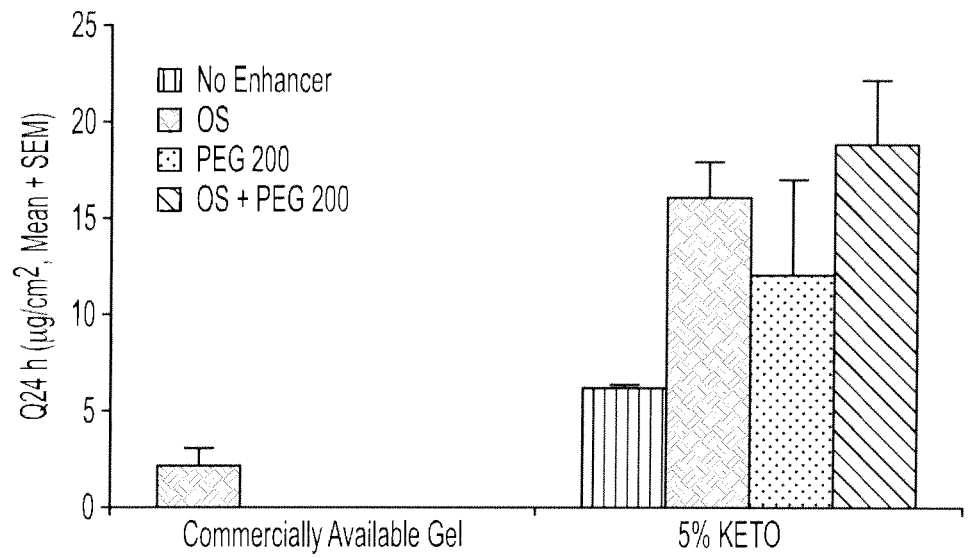
Figure 8: Permeation of KETO transdermal spray in comparison with a commercially available gel. Formulations contain 5% KETO, 0 or 5% OS, 0 or 2.5% PEG200 in IPA.
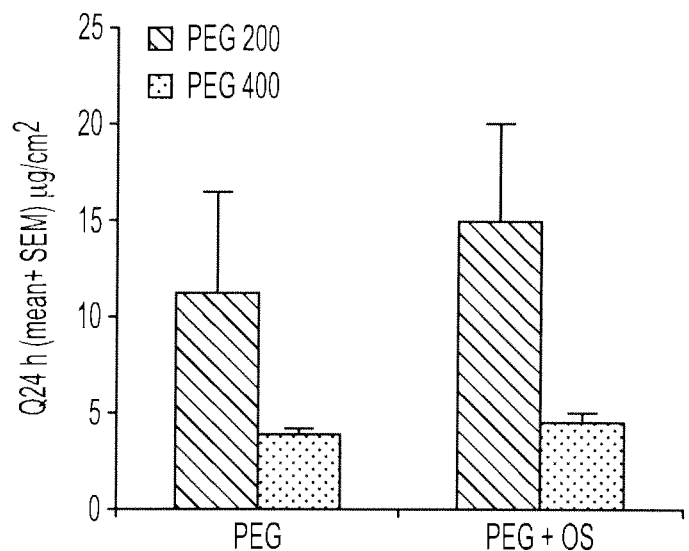
Figure 9: 2.5% KETO, 0 or 5% OS, 2.5% PEG200 or PEG400 in IPA.

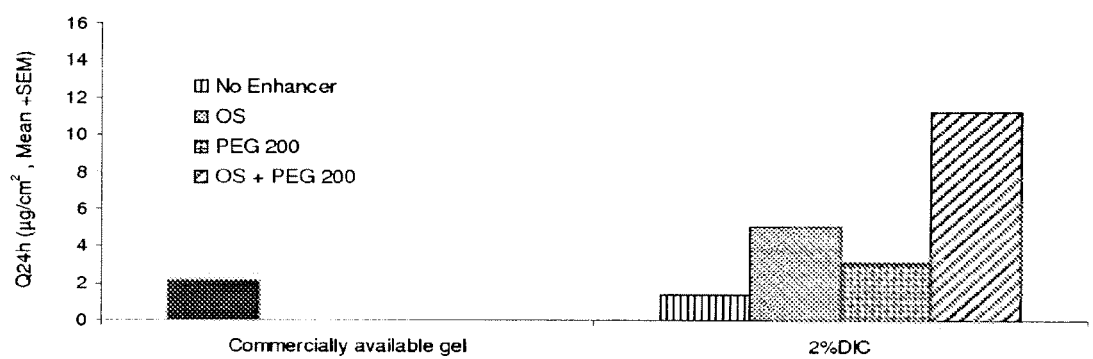
Figure 10: Permeation of Diclofenac transdermal spray (2% DIC diethylamine, 0 or 5% OS, 0 or 2.5% PEG200 in IPA) vs. a commercially available gel

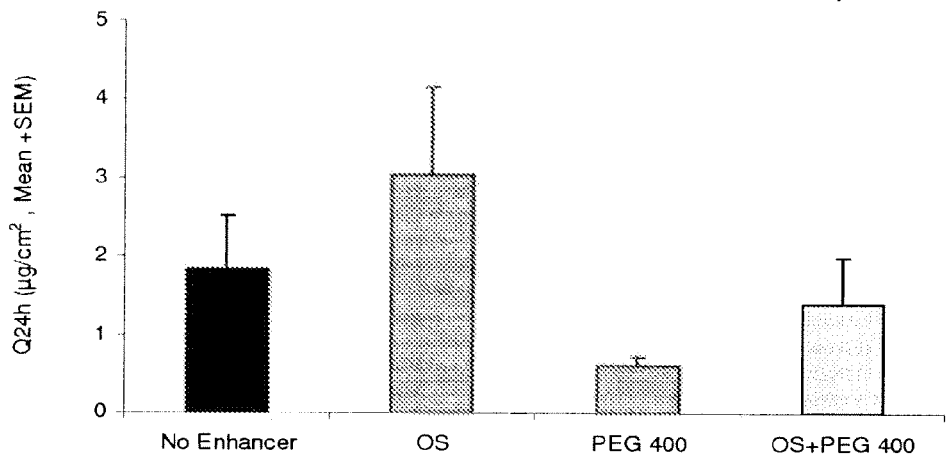
Figure 11: DIC diethylamine from a transdermal spray formulation (1%DIC, 0 or 5%OS, 0 or 2.5%PEG400 in IPA)
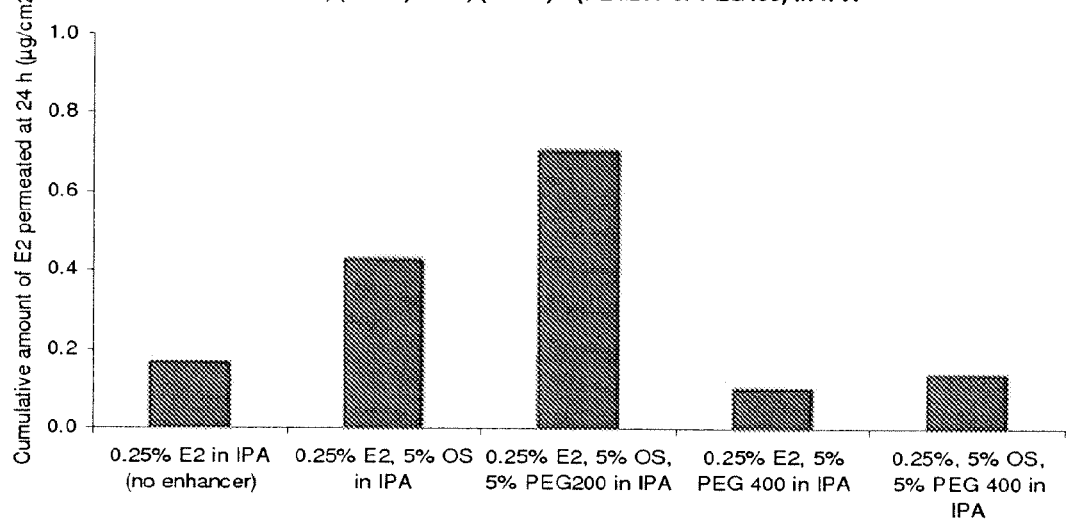
Figure 12: Effect of PEG200 or PEG 400 on Estradiol permeation. Formulations contain 0.25% E2, (0 or 5)% OS, (0 or 5)% (PEG200 or PEG400) in IPA

TRANSDERMAL DELIVERY SYSTEM

FIELD

This invention relates to a transdermal delivery system and to a method of transdermal delivery of a physiologically active agent.

BACKGROUND

Administration of physiologically active agents through the skin ('transdermal delivery') has received increased attention because it not only provides a relatively simple dosage regime but it also provides a relatively slow and controlled route for release of a physiologically active agent into the systemic circulation. However, transdermal drug delivery is complicated by the fact that the skin behaves as a natural barrier and therefore transport of agents through the skin is a complex mechanism.

Structurally, the skin consists of two principle parts, a relatively thin outermost layer (the 'epidermis') and a thicker inner region (the 'dermis'). The outermost layer of the epidermis (the 'stratum corneum') consists of flattened dead cells which are filled with keratin. The region between the flattened dead cells of the stratum corneum is filled with lipids which form lamellar phases that are responsible for the natural barrier properties of the skin.

For effective transdermal delivery of a physiologically active agent that is applied to the surface of the skin ('topical application'), the agent must partition firstly from the vehicle into the stratum corneum, it must typically then diffuse within the stratum corneum before partitioning from the stratum corneum to the viable epidermis.

To overcome some of the problems with transdermal delivery that are associated with transport across the dermal layers ('percutaneous absorption'), physiologically active agents are commonly formulated with dermal penetration enhancers (Finnin and Morgan, J. Pharm. Sci., Vol 88, No. 10, October 1999, pp 955-958) which are often lipophilic chemicals that readily partition into the stratum corneum whereupon they exert their effects on improving the transport of drugs across the skin barrier.

A transdermal "patch" typically consists of a matrix or reservoir containing the drug to be administered, together with a backing layer, an adhesive and a protective release liner. Release membranes may also be incorporated. The delivery of drugs through these systems is either through passive diffusion, controlled by a semi-permeable release membrane, or is controlled by the adhesive/adhesive matrix. The system may also incorporate drug penetration enhancers to increase the flux of the drug through the skin.

One of the drawbacks of the current approaches is that the formulations are typically in continuous contact with the skin. Creams and ointments or adhesives used in patches can cause skin irritation and sensitisation. A significant proportion of patch users suffer from skin irritation and sensitisation due to adhesives used in the patch.

The rate of drug delivery across a dermal surface can be increased by dermal penetration enhancers. The problem with most known dermal penetration enhancers is that they are often toxic, irritating or allergenic. These enhancers tend to be proton accepting solvents such as dimethylsulfoxide and dimethyacetamide. More recently, 2-pyrrolidine, N,N diethyl-m-toluamide (Deet), 1-dodecal-azacycloheptane-2-one (Azone), N,N dimethylformamide, N-methyl-2-pyrrolidine and calcium thioglycolate have been reported as effective enhancers. However, difficulties remain with such dermal enhancers because the problem of irritation at the site of application has not been overcome.

The most critical problem with these compounds however is their toxicity. If a compound when used as a dermal enhancer is toxic, irritating or allergenic, then that compound is unsuitable for application to the animal body. Dimethyl acetamide is not clinically acceptable for these reasons. Although Deet and Azones have lower reported toxicities, their toxicity is still such that they are not widely used. It is possible that Azone and dimethyl sulfoxide may be employed as a dermal penetration enhancer if the amount applied is sufficiently small so as not to be appreciably toxic, irritating or allergenic to the animal.

The compositions of the present invention are suitable for use as vehicles for the topical application of specific compounds to the skin using pharmaceutical, nutraceutical, cosmetic or veterinary preparations. Such topical application enables the specific compounds to penetrate the skin and enter the circulatory system thereby enabling the active compound (s) to have a systemic effect. The at least one active compound may be a pharmacologically active compound. A "pharmacologically active compound" is a compound that has a therapeutic effect on the human or animal body in the treatment or prevention of a condition.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY

The invention provides a transdermal delivery system comprising composition comprising a physiologically active agent and a penetration enhancer wherein the penetration enhancer comprises a combination of (i) an ester of salicylic acid, preferably selected from the $C_6$ to $C_{30}$ aliphatic ester of salicylic acid and (ii) polyethylene glycol of average molecular weight no more than 300.

In a further aspect the invention provides a method of transdermal administration of an active agent to an animal subject, including a human, comprising application to dermal surface of the animal of the above described transdermal delivery system.

In yet another aspect the invention provides use of (i) an ester of salicylic acid, preferably selected from the $C_6$ to $C_{30}$ aliphatic ester of salicylic acid and (ii) polyethylene glycol (of average molecular weight no more than 300) in manufacture of a medicament with a physiologically active agent for transdermal administration of the physiologically active agent to an animal by application of the medicament to an area of the skin surface of the animal.

In a further aspect the invention provides a method of preparing a transdermal delivery system for administration to an area of dermal surface of an animal the method comprising combining the physiologically active agent and a first penetration enhancer component of an ester of salicylic acid, preferably selected from the $C_6$ to $C_{30}$ aliphatic ester of salicylic acid and a second penetration enhancer component of polyethylene glycol of average molecular weight no more than 300.

In a further embodiment the invention comprises a transdermal delivery system comprising a spray apparatus comprising a container for a transdermal composition a spray nozzle and an actuator for delivering a metered dose of spray from the container via the nozzle, wherein the transdermal composition comprises a physiologically active agent and a first penetration enhancer component of an ester of salicylic acid, preferably selected from the $C_6$ to $C_{30}$ aliphatic ester of salicylic acid, and a second penetration enhancer component of polyethylene glycol of average molecular weight no more than 300.

The transdermal delivery system will preferably be applied in a dose sufficient to provide an effective amount of the physiologically active agent in the bloodstream of the animal.

Preferably the animal is a human but the invention also extends to the treatment of non-human animals.

DEFINITIONS

It will be understood by those skilled in the art that the term polyethylene glycol does not include diethylene glycol (although diethylene glycol may if desired be present as an additional component). Polyethylene glycol of average molecular weight no more than 300 includes polyethylene glycol of nominal average molecular weight 200 and 300 wherein the average molecular weight is not more than 110% and not less than 90% (preferably not more than 105% and not less than 95%) of the nominated value. Polyethylene glycol is of formula $H—[OCH_2CH_2]_n—OH$. An average molecular weight of no more than 300 means the average value of n is at least 3 and is generally from 3 to 6 such as 3, 4, 5 or 6 (although the average need not be an integer) and more preferably 3 to 5. Polyethylene glycol (PEG) is widely available from commercial suppliers in pharmaceutical grades and is sold in specified nominal molecular weights which generally signify that the average molecular weight is not more than 105% and not less than 95% of the nominated value. The viscosities and methods for molecular weight determination are disclosed in USP NF Official Compendium of Standards Volume 11180-1182 [2007 Edition].

The term “physiologically active agent” is used herein to refer to a broad class of useful chemical and therapeutic agents.

The term “physiologically active” in describing the agents contemplated herein is used in a broad sense to comprehend not only agents having a direct pharmacological effect on the host, but also those having an indirect or observable effect which is useful in the medical arts. The term physiologically active agent includes prodrugs of the agent which in vivo exerts the physiological effect.

Steroids encompass compounds having the general cyclopentanoperhydrophenanthrene ring system of formula:

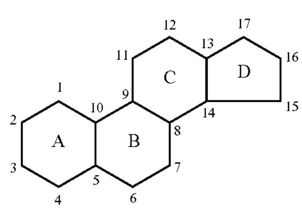

Steroids vary by the functional groups attached to these rings and the oxidation state of the rings. The steroid may be in the form of the active drug or may be a prodrug steroid which in vivo provides a more active form of the steroid. The steroids include drugs and prodrugs which provide eutrogenic, androgenic glucocorticoid, adrenocortoid, anabolic or birth control activity. Examples of steroids include, for example, dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolone hexacetonide, triamcinolone diacetate, methylprednisolone, methylprednisolone acetate, methylprednisolone sodium succinate, flunsolide, beclomethasone dipropionate, betamethasone sodium phosphate, betamethasone, vetamethasone disodium phosphate, vetamethasone sodium phosphate, betamethasone acetate, betamethasone disodium phosphate, chloroprednisone acetate, corticosterone, desoxycorticosterone, desoxycorticosterone acetate, desoxycorticosterone pivalate, desoximethasone, estradiol, fludrocortisone, fludrocortisone acetate, dichlorisone acetate, fluorohydrocortisone, fluorometholone, fluprednisolone, paramethasone, paramethasone acetate, androsterone, flu oxymesterone, aldosterone, methandrostenolone, methylandrostenediol, methyl testosterone, norethandrolone, testosterone, testosterone enanthate, testosterone propionate, equilenin, equilin, estradiol benzoate, estradiol dipropionate, estriol, estrone, estrone benzoate, acetoxypregnenolone, anagestone acetate, chlormadinone acetate, flurogestone acetate, hydroxymethylprogesterone, hydroxymethylprogesterone acetate, hydroxyprogesterone, hydroxyprogesterone acetate, hydroxyprogesterone caproate, melengestrol acetate, normethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, hydrocortisone sodium succinate, methylprednisolone sodium succinate, prednisolone phosphate sodium, triamcinolone acetonide, hydroxydione sodium, spironolactone, oxandrolone, oxymetholone, prometholone, testosterone cypionate, testosterone phenylacetate, estradiol cypionate, and norethynodrel.

A “prodrug” is a pharmaceutically active agent which is administered in an inactive or less active form and is metabilised into an active form. The prodrug itself may have little or none of the desired activity until it interacts with the systems of the body such as the skin or circulatory systems. Nonetheless a pharmaceutically active agent used in the transdermal delivery system of the invention include agents which are prodrugs which on administration form a more active agent in vivo during or after the process of transdermal administration.

In yet another preferred embodiment, a prodrug or a composition of prodrug mixed with the parent composition has a permeation rate that is faster or slower than an identical composition having a pharmacologically equivalent amount of the parent drug. In still another preferred embodiment, the composition has a duration of the therapeutic effect that is longer or shorter than a composition having a pharmacologically equivalent amount of the parent drug alone. In another preferred embodiment, the prodrug is more lipophilic than the parent drug and the prodrug has a greater permeation rate through the skin. Generally prodrugs are variations or derivatives of the parent drugs which have groups cleavable under metabolic conditions. Prodrugs become the parent drugs which are pharmaceutically active or more active in vivo, when they undergo solvolysis under physiological conditions or undergo enzymatic degradation. Prodrugs commonly known in the art include acid esters prepared by reaction of the parent acids or alcohol with a suitable alcohol or acid respectively, or amides prepared by reaction of the parent acid or amine compound with an amine or acid respectively, or basic groups reacted to form an acylated base derivative. Examples of prodrugs are discussed in, Bundgard, Design of Prodrugs, pp. 7-9, 21-24, Elsevier, Amsterdam 1985; Silverman, The Organic Chemistry of Drug Design and Drug Action, pp. 352-401, Academic Press, San Diego, Calif., 1992 and Burger's Medicinal Chemistry and Drug Chemistry, Fifth Ed., Vol. 1, pp. 172-178, 949-982 (1995). The other method for controlling the blood plasma profile of subject is in the selection of the prodrug, such as based on its molecular weight or polarity. By increasing the molecular weight of the prodrug, the time to the onset of permeation of effective amounts of the prodrug will increase relatives to the parent drug. One example of this effect is in the use of norethindrone and norethindrone acetate. The permeation rate of norethindrone rapidly peaks after application, whereas norethindrone acetate having a higher molecular weight reaches a maximum after the norethindrone permeation rate begins to decline. steroids having a free hydroxy group at a position on the steroid ring, such as the 17-position, the 3-position, or at the 11-position on the fused ring. Particularly preferred are steroidal hormones such as estrogens, progestins, and androgens. The corresponding steroid prodrug (prosteroid) is defined as a corresponding structure to the steroid where the free hydroxy at the 3, 11 or 17 position has been reacted with an alcohol reactive moiety. Particularly preferred are steroid derivatives acylated at the 17 position hydroxyl for example by a C1-C12 alkanoyl group. Regardless of whether the steroid or the corresponding prosteroid derivative is incorporated in the carrier composition as the dominant drug, each provides a source of steroid in the bloodstream to achieve the intended physiological effect which, in the case of the corresponding prosteroid, occurs through metabolic conversion of the derivative. A steroid ester is the corresponding structure to the steroid where the free hydroxy group on the ring has been esterified. Examples of a steroid and its corresponding ester include estradiol and estradiol benzoate, estradiol 17-beta cypionate, estradiol 17 propionate, estradiol hemisuccinate (eutocol), estradiol enanthate, estradiol undecylate, estradiol acetate, and estradiol proprionate, etc. Another example is testosterone and its corresponding ester of testosterone such as 17 beta-cypionate, testosterone enanthate, testosterone nicotinate, testosterone phenylacetate, testosterone proprionate, etc. Also included are non-esters that have groups on the 17 position such as testosterone 17-chloral hemiacetal, or ethers that have groups on the 3-position such as estradiol 3-methyl ether.

The terms "percutaneous" and "transdermal" are used herein in the broadest sense to refer to being able to pass through unbroken skin.

The term "dermal penetration enhancer" is used herein in its broadest sense to refer to an agent which improves the rate of percutaneous transport of active agents across the skin for use and delivery of active agents to organisms such as animals, whether it be for local application or systemic delivery.

The term "non-occlusive" is used herein in its broadest sense to refer to not trapping or closing the skin to the atmosphere by means of a patch device, fixed reservoir, application chamber, tape, bandage, sticking plaster, or the like which remains on the skin at the site of application for a prolonged length of time. It is particularly preferred that the transdermal delivery system of the invention is non-occlusive.

The term "stratum corneum" is used herein in its broadest sense to refer to the outer layer of the skin, which is comprised of (approximately 15) layers of terminally differentiated keratinocytes made primarily of the proteinaceous material keratin arranged in a 'brick and mortar' fashion with the mortar being comprised of a lipid matrix made primarily from cholesterol, ceramides and long chain fatty acids. The stratum corneum creates the rate limiting barrier for diffusion of the active agent across the skin.

The term "skin-depot" is used herein in its broadest sense to refer to a reservoir or deposit of active agent and dermal penetration enhancer within the stratum corneum, whether it be intra-cellular (within keratinocytes) or inter-cellular.

The term "volatile:non-volatile liquid vehicle" is used in the art to refer to a liquid pharmaceutical vehicle comprising a volatile liquid mixed with a non-volatile liquid vehicle, such as a dermal penetration enhancer. A system or vehicle comprising a volatile liquid mixed with a non-volatile dermal penetration enhancer when described herein is used in its broadest sense to include those systems known as volatile:non-volatile liquid vehicles.

The term "aliphatic" includes straight chain, branched chain and cyclic aliphatic and may be saturated alkyl groups or unsaturated aliphatic containing from 1 to 3 unsaturated groups particularly 1 to 3 double bonds.

The transdermal drug delivery system of the present invention enables a wide range of physiologically active agents to be delivered through the skin to achieve a desired systemic effect. The drug delivery system preferably comprises the active agent intimately mixed with a non-volatile dermal penetration enhancer and a volatile liquid. Where the drug delivery system is applied to the skin, the active agent and non-volatile liquid are thermodynamically driven into the skin as the volatile liquid evaporates. Once within the skin the non-volatile liquid may either disrupt the lipid matrix and/or act as a solubilizer to allow an enhanced penetration rate of the active agent through the skin and into the subject being treated. In this way, the dermal penetration enhancer acts as a vehicle and many systemic active agents are able to be transdermally administered to an animal.

A "nutraceutically active compound" is a compound, derived from a natural origin (animal or vegetable) that has a beneficial and/or therapeutic effect on the human or animal body in the treatment of a condition. Such compounds may be regarded as nutrients.

Throughout the description and the claims of this specification the word "comprise" and variations of the word, such as "comprising" and "comprises" is not intended to exclude other additives, components, integers or steps.

DETAILED DESCRIPTION

The present inventors have found that the use of a penetration enhancer which is a combination of (i) an ester of salicylic acid, preferably selected from the $C_6$ to $C_{30}$ aliphatic esters of salicylic acid and (ii) polyethylene glycol (of average molecular weight no more than 300) shows a synergistic improvement in penetration enhancement.

The weight ratio of ester of salicylic acid to polyethylene glycol (of average molecular weight no more than 300) is preferably in the range of from 95:5 to 5:95 and preferably from to 1:10 to 10:1 such as 1:10 to 5:1 and 1:5 to 2:1. The optimal ratio may vary depending on the nature and concentration of the active agent and the concentration of the penetration enhancer combination.

The ester of salicylic acid is preferably a $C_6$ to $C_{18}$ aliphatic ester, more preferably a $C_6$ to $C_{12}$ alkyl ester and still more preferably is $C_8$ alkyl and most preferably is 2-ethylhexylester known by the common name Octyl salicylate or simply Octisalate.

Typically the ester of salicylic acid will be present in an amount of from 0.1 to 10% by weight of the total transdermal composition of the invention and more preferably from 0.5 to 5% such as 0.5, 0.7, 0.8, 0.9, 1.0, 1.2, 1.5, 1.7, 2.0, 3.0, 3.5, 4.0, 4.5 and 5.0.

Typically the PEG of average molecular weight less than 300 will be present in an amount in the range of from 0.1 to 40% by weight of the total composition and preferably from 0.5 to 20% such as 1%, 1.5%, 2%, 2.5%, 3%, 3.5%, 4%, 4.5%, 6%, 7%, 8%, 9%, 10%, 11%, 12%, 13%, 14%, 15%, 16%, 17%, 18%, 19%, 20%.

The composition of the invention preferably comprises PEG 200 in an amount in the range of from 0.1 to 40% by weight of the total composition and preferably from 0.5 to 20% such as 1%, 1.5%, 2%, 2.5%, 3%, 3.5%, 4%, 4.5%, 6%, 7%, 8%, 9%, 10%, 11%, 12%, 13%, 14%, 15%, 16%, 17%, 18%, 19%, 20%.

The composition of the invention may and preferably will contain a volatile solvent. Preferably the volatile solvent has a vapour pressure above 35 mm Hg at atmospheric pressure and normal skin temperature of 32 degrees Celsius. In a particularly preferred form of the invention the solvent preferably a $C_2$ to $C_4$ alkanol and more preferably is ethanol or isopropanol, or a mixture thereof.

Known dermal penetration enhancers may also be employed in the transdermal drug delivery system. The use of known dermal penetration enhancers include laurocapram (Azone™) and laurocapram derivatives, such as those 1-alkylazacycloheptan-2-ones specified in U.S. Pat. No. 5,196,410, and oleic acid and its ester derivatives, such as methyl, ethyl, propyl, isopropyl, butyl, vinyl and glycerylmonooleate, and sorbitan esters such as sorbitan monolaurate and sorbitan monooleate, and other fatty acid esters such as isopropyl laurate, isopropyl myristate, isopropyl palmitate, diisopropyl adipate, propylene glycol monolaurate and propylene glycol monooleate, and long chain alkyl esters of 2-pyrrolidone, particularly the 1-lauryl, 1-hexyl and 1-(2-ethylhexyl) esters of 2-pyrollidone and those dermal penetration enhancers given in U.S. Pat. No. 5,082,866, particularly dodecyl (N,N-dimethylamino) acetate and dodecyl (N,N-dimethylamino) propionate and in U.S. Pat. No. 4,861,764, particularly 2-n-nonyl-1-3-dioxolane. Preferably the composition will comprise no more than 5% by weight of the non-volatile penetration enhancers other than PEG and the salicylic acid esters more preferably no more than 1% and most preferably no more than 0.5% by weight of the composition of non-volatile penetration enhancers other than PEG of molecular weight of no more than 300 and salicylic acid esters.

The volatile solvent is preferably present in the composition of the invention in an amount in the range of from 40 to 95% by weight of the composition and more preferably from 50 to 95%, still more preferably from 60 to 95% by weight such as 65% to 95% by weight 70% to 95%, 70 to 90% and 75 to 90% by weight of the total composition.

The composition of the invention may if desired contain one or more additional adjuvants such as those selected from the group consisting of penetration enhancers, surfactants, thickeners and solvents. Examples of suitable thickeners include polyacrylic acids; and acylic acid copolymers agor, carrageenan, food starch, gelatins, germ Arabic, guorgem, hydroxyethyl cellulose hydroxypropymethyl cellulose, protein and polyvinyl pyrrolidone. The content of thickener may be from 0 to 5%. It is however a particularly preferred aspect of the invention that the composition consists essentially of:
 (i) an physiologically active agent component which may include one or more physiologically active agents;
 (ii) a penetration enhancer component consisting of an ester of salicylic acid and a polyethylene glycol of average molecular weight no more than 300;
 (iii) a volatile solvent consisting of one or more of ethanol and isopropanol; and
 (iv) optionally a propellant.

It will be understood by those skilled in the art that alcohols and polyols contain a certain amount of water. Typically the total water content of the composition is less than 20% by weight and preferably less than 10% by weight of the total composition.

The composition of the invention may be in a range of forms from a liquid, cream, paste, gel, lotion, patch (matrix and reservoir), tape, plaster or film former. In the more preferred embodiment the transdermal delivery system is in the form of a liquid for application to a defined area of skin.

The compositions of the present invention may be in any form suitable for topical application to the skin. Suitable forms include sprayable liquids; gels; liquids that may be applied using a roll-on device; lacquers; and sustained release matrices of transdermal delivery devices such as patches. The compositions are usually administered alone but, under some circumstances, administration may be further modified by using other delivery mechanisms such as iontophoresism, ultrasound and microneedles to enhance penetration. Non-occlusive application and in particular Spray application are preferred.

Suitable pharmacologically active compounds may be selected from:

Alimentary System Antidiarrhoeals such as diphenoxylate, loperamide andhyoscyamine;

Cardiovascular system agents including:

Antihypertensives such as hydralazine, minoxidil, captopril, enalapril, clonidine, prazosin, debrisoquine, diazoxide, guanethine, methyldopa, reserpine, trimetaphan;

Calcium channel blockers such as diltiazem, felodopine, amlodipine, nitrendipine, nifedipine and verapamil;

Proton pump inhibitors such as lansoprazole; omeprazole; and pantaprazole;

Antiarrhyrthmics such as amiodarone, flecainide, disopyramide, procainamide, mexiletene and quinidine;

Antiangina agents such as glyceryl trinitrate, erythritol tetranitrate, pentaerythritol tetranitrate, mannitol hexanitrate, perhexilene, isosorbide dinitrate and nicorandil;

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate;

Cardiotonic glycosides such as digoxin and other cardiac glycosides and theophylline derivatives;

Adrenergic stimulants such as adrenaline, ephedrine, fenoterol, isoprenaline, orciprenalihe, rimeterol, salbutamol, salmeterol, terbutaline, dobutamine, phenylephrine, phenylpropanolamine, pseudoephedrine and dopamine;

Vasodilators such as cyclandelate, isoxsuprine, papaverine, dipyrimadole, isosorbide dinitrate, phentolamine, nicotinyl alcohol, co-dergocrine, nicotinic acid, glyceryl trinitrate, pentaerythritol tetranitrate and xanthinol; and Antimigraine preparations such as ergotamine, dihydroergotamine, methysergide, pizotifen and sumatriptan.

Drugs affecting blood and haemopoietic tissues including:

Anticoagulants and thrombolytic agents such as warfarin, dicoumarol, low molecular weight heparins such as enoxaparin; streptokinase and its active derivatives.

Haemostatic agents such as aprotinin, tranexamic acid and protamine.

Drugs affecting the Central Nervous System including:

Analgesics;

antipyretics including the opiod analgesics such as buprenorphine, dextromoramide, dextropropoxyphene, fentanyl, alfentanil, sufentanil, hydromorphone, methadone, morphine, oxycodone, papaveretum, pentazocine, pethidine, phenoperidine, codeine and dihydrocodeine. Others include acetylsalicylic acid (aspirin), paracetamol, and phenazone;

Hypnotics and sedatives such as the barbiturates, amylobarbitone, butobarbitone and pentobarbitone and other hypnotics and sedatives such as choral hydrate, chlormethiazole, hydroxyzine and meprobamate; and Antianxiety agents such as the benzodiazepines, alprazolam, bromazepam, chlordiazepoxide, clobazam, chlorazepate, diazepam, flunitrazepam, flurazepam, lorazepam, nitrazepam, oxazepam, temazepam and triazolam.

Agents to treat food allergies such as sodium cromoglicate.

Neuroleptic and antipsychotic drugs such as the phenothiazines, chlorpromazine, fluphenazine, pericyazine, perphenazine, promazine, thiopropazate, thioridazine and trifluoperazine and the butyrophenones, droperidol and haloperidol and the other antipsychotic drugs such as pimozide, thiothixene and lithium.

Antidepressants such as the tricyclic antidepressants amitryptyline, clomipramine, desipramine, dothiepin, doxepin, imipramine, nortriptyline, opipramol, protriptyline and trimipramine; tetracyclic antidepressants such as mianserin; monoamine oxidase inhibitors such as isocarboxazid, phenelizine, tranylcypromine and moclobemide; selective serotonin re-uptake inhibitors such as fluoxetine, paroxetine, titalopram, fluvoxamine and sertraline; and tetracyclic antidepressants such as mirtazapine and any metabolites, salts enantiomers (including esmirtazapine), solvants, non-covalent complexes, chelates, hydrates, crystalline or amorphous forms thereof.

CNS stimulants such as caffeine.

Anti-alzheimer's agents such as tacrine.

Antiparkinson agents such as amantadine, benserazide, carbidopa, levodopa, benztropine, biperiden, benzhexyl, procyclidine and dopamine-2 agonists such as S(−)-2-(N-propyl-N-2-thienylethylamino)-5-hydroxytetralin (N-0923).

Lipid regulating drugs such as statins.

Drugs affecting bone metabolism such as calcitonin and bisphosphonates.

Anticonvulsants such as phenyloin, valproic acid, primidone, phenobarbitone, methylphenobarbitone and carbamazepine, ethosuximide, methsuximide, phensuximide, sulthiame and clonazepam.

Antiemetics, antinauseants such as the phenothiazines, prochloperazine, thiethylperazine and 5HT-3 receptor antagonists such as ondansetron and granisetron and others such as dimenhydrinate, diphenhydramine, metoclopramide, domperidone, hyoscine, hyoscine hydrobromide, hyoscine hydrochloride, clebopride and brompride.

Musculoskeletal system drugs:

Non-steroidalanti-inflammatory agents including their racemic mixtures or individual enantiomers where applicable, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol and ketoralac;

Additional non-steroidal antiinflammatory agents which can be formulated in combination with the dermal penetration enhancers include salicylamide, salicylic acid, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloide, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;

Antirheumatoid agents such as penicillamine, aurothioglucose, sodium aurothiomalate, methotrexate and auranofin;

Muscle relaxants such as baclofen, diazepam, cyclobenzaprine hydrochloride, dantrolene, methocarbamol, orphenadrine and quinine; and Agents used in gout and hyperuricaemia such as allopurinol, colchicine, probenecid and sulphinpyrazone.

Hormones and Steroids including;

Estrogens such estradiol, estriol, estradiol benzoate, estradiol 17. beta.-cypionate, estradiol enanthate, estradiol propionate, estrone, ethinylestradiol, Fosfestrol, Dienestrol mestranol, stilboestrol, dienoestrol, epioestriol, estropipate Diethylstilbestrol, Chlorotrianisene, conjugated estrogenic hormones, Polyestradiol phosphate and zeranol and mixtures thereof;

Progesterone and progestins such as norethisterone, norethisterone acetate, gestodene, levonorgestrel, allylestrenol, anagestone, desogestrel, dimethisterone, dydrogesterone, ethisterone, ethynodiol, Ethynodiol diacetate, Etonogestrel, gestodene, ethinylestradiol, haloprogesterone, 17-hydroxy-16-methylene-progesterone, 17. alpha.-hydroxyprogesterone, lynestrenol, medroxyprogesterone, melengestrol, norethindrone, norethynodrel, norgesterone, Gestonorone, Norethisterone, norgestimate, norgestrel, Levonorgestrel, norgestrienone, norvinisterone, pentagestrone, MENT (7-methyl-19-testosterone); Norelgestromin, and trimigestone Drospirenone, Tibolone, and megestrol and mixtures thereof;

Antiandrogens such as cyproterone acetate and danazol;

Antiestrogens such as tamoxifen and epitiostanol and the aromatase inhibitors, exemestane and 4-hydroxy-androstenedione and its derivatives;

Androgens and anabolic agents such as androisoxazole, androstenediol, bolandiol, bolasterone, clostebol, ethylestrenol. formyldienolone, 4-hydroxy-19-nortestosterone, methandriol, methenolone, methyltrienolone, nandrolone, norbolethone, oxymesterone, stenbolone and trenbolone. Androgenic steroids can include boldenone, fluoxymesterone, mestanolone, mesterolone, methandrostenolone, 17-methyltestosterone, 17. alpha-methyltestosterone 3-cyclopentyl enol ether, norethandrolone, normethandrone, oxandrolone, oxymesterone, oxymetholone, prasterone, stanlolone, stanozolol, testosterone, testosterone 17-chloral hemiacetal, testosterone proprionate, testosterone enanthate tiomesterone dehydroepiandrosterone (DHEA), androstenedione (Andro): an androstenediol, androsterone, dihydrotestosterone (DHT) and androstanolone and derivatives thereof;

5-alpha reductase inhibitors such as finasteride, turosteride, LY-191704 and MK-306;

Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate methylprednisolone, prednisolone, prednisolone 21-phosphate, prednisone, triamcinolone, triamcinolone acetonide;

Further examples of steroidal antiinflammatory agents for use in the instant compositions include cortodoxone, fluoracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol;

Pituitary hormones and their active derivatives or analogs such as corticotrophin, thyrotropin, follicle stimulating hormone (FSH), luteinising hormone (LH) and gonadotrophin releasing hormone (GnRH);

Hypoglycaemic agents such as insulin, chlorpropamide, glibenclamide, gliclazide, glipizide, tolazamide, tolbutamide and metformin;

Thyroid hormones such as calcitonin, thyroxine and liothyronine and antithyroid agents such as carbimazole and propylthiouracil; and Other miscellaneous hormone agents such asoctreotide.

Pituitary inhibitors such as bromocriptine.

Ovulation inducers such as clomiphene.

Genitourinary system including:

Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potassium sparing diuretics, spironolactone, amiloride and triamterene.

Antidiuretics such as desmopressin, lypressin and vasopressin including their active derivatives or analogs.

Obstetric drugs including agents acting on the uterus such as ergometrine, oxytocin and gemeprost.

Prostaglandins such as alprostadil (PGEi), prostacyclin (PGI2), dinoprost (prostaglandin F2-alpha) and misoprostol.

Antimicrobials including:

Antimicrobials including the cephalosporins such ascephaiexin, cefoxytin and cephalothin;

Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, mezlocillin, piperacillin, ticarcillin and azlocillin;

Tetracyclines such as minocycline, chlortetracycline, tetracycline, demeclocycline, doxycycline, methacycline and oxytetracycline and other tetracycline-type antibiotics;

Aminoglycosides such as amikacin, gentamicin, kanamycin, neomycin, netilmicin and tobramycin;

Antifungals such as amorolfine, isoconazole, clotrimazole, econazole, miconazole, nystatin, terbinafine, bifonazole, amphotericin, griseofulv in, ketoconazole, fluconazole and flucytosine, salicylic acid, fezatione, ticlatone, tolnaftate, triacetin, zinc, pyrithione and sodium pyrithione;

Quinolones such as nalidixic acid, cinoxacin, ciprofloxacin, enoxacin and norfloxacin;

Sulphonamides such as phthalylsulphthiazole, sulfadoxine, sulphadiazine, sulphamethizole and sulphamethoxazole;

Sulphones such as dapsone; and

Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonam, colistin IV, metronidazole, tinidazole, fusidic acid and trimethoprim; 2-thiopyridine N-oxide; halogen compounds, particularly iodine and iodine compounds such as iodine-PVP complex and diiodohydroxyquin; hexachlorophene; chlorhexidine; chloroamine compounds; benzoylperoxide.

Antituberculosis drugs such as ethambutol, isoniazid, pyrazinamide, rifampicin and clofazimine.

Antimalarials such as primaquine, pyrimethamine, chloroquine, hydroxychloroquine, quinine, mefloquine and halofantrine.

Antiviral agents such as acyclovir and acyclovir prodrugs, famciclovir, zidovudine, didanosine, stavudine, lamivudine, zalcitabine, saquinavir, indinavir, ritonavir, ndocosanol, tromantadine and idoxuridine.

Anthelmintics such as mebendazole, thiabendazole, niclosamide, praziquantel, pyrantel embonate and diethylcarbamazine.

Cytotoxic agents such as plicamycin, cyclophosphamide, dacarbazine, fluorouracil and its prodrugs [described, for example, in international Journal of Pharmaceutics 111, 223-233 (1994)], methotrexate, procarbazine, 6-mercaptopurine and mucophenolic acid.

Metabolism agents including:

Anorectic and weight reducing agents including dexfenfluramine, fenfluramine, diethylpropion, mazindol and phentermine; and Agents used in hypercalcaemia such as calcitriol, dihydrotachysterol and their active derivatives or analogs;

Respiratory system agents including:

Antitussives such as ethylmorphine, dextromethorphan and pholcodine;

Expectorants such as acetylcysteine, bromhexine, emetine, guaiphenesin, ipecacuanha ans saponins;

Decongestants such as phenylephrine, phenylpropanolamine ans pseudoephedrine; and Bronchospasm relaxants such as ephedrine, fenoterol, orciprenaline, rimiterol, salbutamol, sodium cromoglycate, cromoglycic acid and its prodrugs (described, for example, in International Journal of Pharmaceutics 7, 63-75 (1980)], terbutaline, ipratropium bromide, salmeterol and theophylline and theophylline derivatives.

Allergy and immune system agents including:

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine.

Local anaesthetics such as bupivacaine, amethocaine, lignocaine, cinchocaine, dibucaine, mepivacaine, prilocalne and etidocaine.

Stratum corneum lipids, such as ceramides, cholesterol and free fatty acids, for improved skin barrier repair [Man, et al. J. Invest. Dennatol., 106(5), 1096, 1996].

H2-receptor antagonists such as cimetidine; and ranitidine;

Neuromuscular blocking agents such assuxamethonium, alcuronium, pancuronium, atracurium, gallamine, tubocurarine and vecuronium.

Smoking cessation agents such as nicotine, bupropion and ibogaine.

Insecticides and other pesticides which are suitable for local or systemic application.

Dermatological agents, such as vitamins A and E, vitamin E acetate and vitamin E sorbate.

Allergens for desensitisation such as house dust mite allergen.

nutraceutically active compounds include carotenoids such as lycopene, lutein, astaxanthin and [beta]-carotene; glucosamine or N-acylglucosamine; ubiquinone;—Vitamins such as vitamins A, C, D and E; Rosmarinic acid; Honokiol; Magnolol; Chlorogenic acid; Oleuropein; Methylsulphonylmethane ("MSM"); Collagen and Chondroitin; Boswellin and boswellic acid;

Keratolytics such as thealpha-hydroxy acids, glycollic acid and salicylic acid.

Psychicenergisers, such as 3-(2-aminopropyl)indole, 3-(2-aminobutyl)indole, and the like.

Anti-acne agents such as isotretinoin, tretinoin and benzoyl peroxide.

Anti-psoriasis agents such as etretinate, cyclosporin and calcipotriol.

Anti-itch agents such as capsaicin and its derivatives such as nonivamide [Tsai, et al. Drug. Dev. Ind. Pharm., 20(4), 719, 1994].

Anticholinergic agents, which are effective for the inhibition of axillary sweating and for the control of prickly heat. The antiperspirant activity of agents such as methatropine nitrate, propantheline bromide, scopolamine, methscopolamine bromide, and the new class of soft antiperspirants, quaternary acyloxymethylammonium salts [described, for example, by Bodor et al, J. Med. chem. 23, 474 (1980) and also in United Kingdom Specification No. 2010270, published 27 Jun. 1979].

The optimal ratio of penetration enhancer to active will differ depending on the nature of the active and the specific identity and composition of the combination which makes up the penetration enhance. Typically the weight ratio of penetration enhancer to active will be in the range of from 1000:1 to 1:1000 and preferably from 500:1 to 1:10 and most preferably from 20:1 to 1:1.

The penetration enhancer of the invention is particularly useful in transdermal administration of antidepressants, women's health actives and hormones. Hormones that may be used in the drug delivery system of the present invention include systemically active hormones which can be delivered through the skin with the assistance of the dermal penetration enhancer to achieve a desired effect.

Suitable hormones include:
androgens such as:
testosterone. dehydroepiandrosterone (DHEA), androstenedione (Andro): an androstenediol, androsterone, dihydrotestosterone (DHT) androstanolone, fluoxymesterone, mesterolone, methyltestosterone and derivatives thereof;
estrogens such as:
Estradiol, Estriol, Estrone, Chlorotrianisene, Dienestrol, Diethylstilbestrol, Ethinylestradiol, Fosfestrol, Mestranol, Polyestradiol phosphate.
Selective estrogen receptor modulators such as:
Bazedoxifene, Clomifene, Fulvestrant, Lasofoxifene, Raloxifene, Tamoxifen, Toremifene Aromatase inhibitor such as:
Aminogluthetimide, Anastrozole, Exemestane, Formestane, Letrozole and Vorozole.
Gonadotropins such as:
Clomifene and Urofollitropin.
Progestogens such as:
progesterone;
progestins such as:
those selected from the group consisting of Desogestrel, Drospirenone, Dydrogesterone, Ethisterone, Etonogestrel, Ethynodiol diacetate, Gestodene, Gestonorone, Levonorgestrel, Lynestrenol, Medroxyprogesterone, Megestrol, Norelgestromin, Norethisterone, Norethynodrel, Norgestimate, Norgestrel, Norgestrienone, ethinylestradiol, Tibolone, megestrol and MENT (7-methyl-19-testosterone);
Selective progesterone receptor modulators such as:
Asoprisnil, CDB-4124
Antiprogestogen such as Mifepristone;
Antigonadotropins such as:
Danazol and Gestrinone; and
GnRH:(receptor) agonis such as:
Buserelin, Goserelin, Histrelin, Leuprorelin, Nafarelin and Triptorelin.
GnRH antagonist: Abarelix, Cetrorelix and Ganirelix.

Compositions of the invention may include a plurality of hormones from one or more of these groups. For example it may be desirable for contraceptive formulations to comprise one or more estrogens and one or more progestins.

The treatment system may be used for local or systemic administration in an effective amount. In one embodiment the transdermal delivery system is administered to provide a pharmaceutically effective amount of the active in the systemic circulation. In one preferred form of the invention the drug delivery system comprises on a weight basis from about 0.1 to about 10% of active agent (partially a hormone), from about 0.1 to 12% of the at least one dermal penetration enhancer and from about 78 to 99.8% ethanol, isopropanol or mixture thereof.

In another preferred form of the invention the drug delivery system comprises, on a weight basis, from about 1 to 3% of a hormone, from about 1 to 15% of the dermal penetration enhancer combination, from about 45 to 90% ethanol, isopropanol or mixture thereof, 5 to 45% water.

Another group of preferred drugs are antidepressants including noradrenergic and specific serotonergic antidepressants ($N_a$SSA); more preferably tetracyclic antidepressants and most preferably mirtazapine and any metabolites, salts, enantiomers (including esmirtazapine), solvants, non-covalent complexes, chelates, hydrates, crystalline or amorphous forms thereof.

Diseases or conditions that may be treated by using the drug delivery system and methods of the present invention include, but are not limited to, male hormone replacement in testosterone deficient hypogonadal men, female hormone replacement therapy for postmenopausal women using for example estradiol, androgen replacement therapy for females lacking libido and/or to treat depression using an androgen such as testosterone, male contraception (for example using a progestin such etonogestrel optionally with testosterone) and female contraception (for example using a progestin optionally in combination with an estrogen). Steroidal hormones particularly estrogens may be used to treat premenstrual syndrome (PMS) symptoms in women for example estradiol. PMS symptoms include (but are not limited to) abdominal bloating, abdominal cramps, headache or migraine, breast tenderness or swelling, anxiety, insomnia, joint or muscle pain and mood swings.

In one embodiment the transdermal delivery system comprises a spray apparatus comprising a container for a transdermal composition, a spray nozzle and an actuator for delivering a metered dose of spray from the container via the nozzle, wherein the transdermal composition comprises a physiologically active agent and a first penetration enhancer component of an ester of salicylic acid, preferably selected from the $C_6$ to $C_{30}$ aliphatic ester of salicylic acid, and a second penetration enhancer component of polyethylene glycol of average molecular weight no more than 300.

The transdermal delivery system will preferably be applied in a dose sufficient to provide an effective amount of the physiologically active agent in the bloodstream of the animal.

Preferably, the applicator provides a metered dose application such as a metered dose aerosol, a stored-energy metered dose pump or a manual metered dose pump. Preferably the drug delivery system is applied to the skin of the animal covering a delivery surface area between about 10 and 800 cm$^2$, more preferably between about 10 and 400$^2$, and most preferably between about 10 and 200 cm$^2$. The application is most preferably performed by means of a topical metered dose spray combined with an actuator nozzle shroud which together accurately control the amount and/or uniformity of the dose applied. One function of the shroud is to keep the nozzle at a pre-determined height above, and perpendicular to, the skin to which the drug delivery system is being applied. This function may also be achieved by means of a spacer-bar or the like. Another function of the shroud is to enclose the area above the skin in order to prevent or limit bounce-back and/or loss of the drug delivery system to the surrounding environment. Preferably the area of application defined by the shroud is substantially circular in shape.

The invention will now be described with reference to the following examples. It is to be understood that the examples are provided by way of illustration of the invention and that they are in no way limiting to the scope of the invention.

EXAMPLES

The compositions of the Examples and their performance are compared with reference to the drawings.

BRIEF DESCRIPTION OF DRAWINGS

In the drawings:

FIG. 1 is a column chart comparing the permeation of a progestin from a control with progestin transdermal delivery composition of the invention of Example 1.

FIG. 2 is a column chart comparing the permeation of an estrogen from a control with a transdermal delivery composition of the invention of Example 1.

FIGS. 3a and 3b are column charts showing the effect on progestin permeation of comparative transdermal compositions containing different progestins and PEG400 rather than PEG 200 as described in Example 2.

FIG. 4 is a column chart comparing the permeation of a progestin from a control composition with a transdermal delivery compositions of the invention containing PEG200 pursuant to Example 2.

FIG. 5 is a column chart comparing the permeation of an estrogen from transdermal delivery compositions 2 to 7 of the invention with the control composition of 1 of Example 2.

FIG. 6 is a column chart comparing the effect of PEG200 on permeation of an androgen from transdermal delivery compositions 1 to 4 of Example 3.

FIG. 7 is a column chart comparing permeation of an androgen from transdermal delivery compositions 2 to 3 with the control composition 1 of Example 4.

FIGS. 8 and 9 are column charts comparing permeation of the non-steroidal anti-inflamatory drug (NASAID) ketoprofen from a commercial product with transdermal delivery spray compositions containing each of OS and PEG alone and in combination (in accordance with the invention) as described in Example 5.

FIGS. 10 and 11 are column charts comparing permeation of the non-steroidal anti-inflamatory drug (NASAID) diclofenac from a commercial product with transdermal delivery spray compositions containing each of OS and PEG200 and PEG 400 alone and OS in combination with the different PEG compositions as described in Example 6.

FIG. 12 is a column chart which compares the effect of each of PEG 200 and PEG 400 on the permeation of the estrogen estradiol from compositions containing OS penetration enhancer as described in Example 7.

Example 1

Investigation of the Effect of PEG200 on Cumulative Norethisterone Acetate and Estradiol Permeation Through Human Skin in Vitro Methods:

Finite-dose in vitro diffusion studies were undertaken using dermatomed human female abdominal skin (500 μm).

These experiments were performed over 24 hours using Franz-type cells. Pre-cut skin membranes were mounted as a barrier between the halves of greased (high vacuum grease, BDH) horizontal Franz-type permeation cells in the middle of the receptor chamber of the cell with the stratum corneum facing the donor chamber. The area available for permeation was approximately 0.925 cm2. The receptor chambers of the permeation cells were filled with the receptor phase (Phosphate Buffered Saline pH 7.4) and capped. The permeation cells were immersed in a constant temperature water bath such that the receptor chambers were maintained at 35° C. Receptor chamber contents were continuously agitated by small PTFE-coated magnetic stirrer bars driven by submersible magnetic stirrers. The skin was allowed to equilibrate to temperature with receptor solution for 1 h in the water bath prior to dosing.

The formulations were applied to the skin at a dose of 3.6 μL/cm2. The applied formulation was spread over the skin area using an Eppendorf positive displacement pipette tip without breaking the skin membrane.

The formulations consisted of:—
Comparison composition 1: 2.8% Norethisterone Acetate (NETA), 0.55% Estradiol (E2), 5% Octyl Salicylate (OS)
Composition 2: 2.8% NETA, 0.55% E2, 5% Polyethylene Glycol 200 (PEG200)
Composition 3: 2.8% NETA, 0.55% E2, 5% OS, 5% PEG200
Composition 4: 2.8% NETA, 0.55% E2, 10% PEG200
Composition 5: 2.8% NETA, 0.55% E2, 5% OS, 10% PEG200

The amount of active that permeated the skin was quantified using validated HPLC methods FIG. 1 compares the penetration of comparative composition 1 with compositions 2-5 relating to invention. PEG200 in combination with OS was found to significantly enhance the permeation of both Norethisterone Acetate and estradiol through human epidermis in vitro. Permeation of NETA is compared in FIG. 1 and permeation of estradiol is compared in FIG. 2.

Example 2

Investigation into the Effect of PEG200 and PEG400 on Cumulative Nestorone & Ethinylestradiol Permeation Through Human Skin In Vitro Methods:

Finite-dose in vitro diffusion studies were undertaken using dermatomed human female abdominal skin (500 μm). These experiments were performed over 24 hours using stainless steel, flow through diffusion cells based on those described previously (Cooper, E. R. J. Pharm. Sci. 1984, 73, 1153-1156) except that the cell was modified to increase the diffusion area to 1.0 cm2. The formulations were applied using a finite dose technique (Franz, T. J. Curr. Probl. Dermatol., 1978, 7, 58-68) to mimic clinical dosing conditions at an applied dose volume of 3.6 μL/cm2. A piece of stainless steel wire mesh was placed directly below the skin in the receptor chamber of the of the diffusion cell to maintain a turbulent flow of receptor solution below the skin. The diffusion cells were maintained at a flow rate of approximately 0.5 mL/hr by a microcassette peristaltic pump (Watson Marlow 505S UK). The cells were kept at 32±0.5° C. by a heater bar and the samples were collected into appropriately sized glass vials for a period of 24 hr. The receptor solutions (Phosphate Buffered Saline pH7.4) maintained sink conditions below the skin.

The formulations consisted of:—
Composition (Camp) 1 (Control): 1.35% Nestorone (NES), 0.35% Ethinylestradiol (EE), 5% Octyl Salicylate (OS) in Isopropyl Alcohol (IPA)
Comp 2: 1.35% NES, 0.35% EE, 5% OS, 5% Polyethylene glycol 400 (PEG400) in IPA
Comp 3: 1.35% NES, 0.35% EE, 0.5% Polyethylene glycol (PEG200) in IPA
Comp 4: 1.35% NES, 0.35% EE, 5% OS, 0.5% PEG200 in IPA
Comp 5: 1.35% NES, 0.35% EE, 1% PEG200 in IPA
Comp 6: 1.35% NES, 0.35% EE, 5% OS, 1% PEG200 in IPA
Comp 7: 1.35% NES, 0.35% EE, 2.5% PEG200 in IPA
Comp 8: 1.35% NES, 0.35% EE, 5% OS, 2.5% PEG200 in IPA
Comp 9: 1.35% NES, 0.35% EE, 5% PEG200 in IPA
Comp 10: 1.35% NES, 0.35% EE, 5% OS, 5% PEG200 in IPA
Comp 11: 1.35% NES, 0.35% EE, 10% PEG200 in IPA
Camp 12: 1.35% NES, 0.35% EE, 5% OS, 10% PEG200 in IPA The amount of active that permeated the skin was quantified using validated HPLC methods The effect of PEG400 on permeation of NES and EE is shown in FIGS. 3a and 3b respectively. PEG200 in combination with OS was found to enhance the permeation of both Nestorone and Ethinylestradiol through human epidermis in vitro.

The addition of PEG400 to the formulation did not have a significant effect (enhancing or inhibitory) on the permeation of Nestorone through human epidermis in vitro. PEG400 was found to inhibit the permeation of ethinylestradiol through human epidermis in vitro.

The effect of PEG 200 in compositions 3 to 12 on permeation of NES is compared with the Composition 1 control (containing no PEG200) in FIG. 4.

The effect of PEG200 in compositions 3 to 12 on permeation of EE is compared with the Composition 1 control in FIG. 5.

Example 3

Investigation into the Effect of PEG200 on Cumulative Testosterone Permeation Through Human Skin In Vitro Methods:

Finite-dose in vitro diffusion studies were undertaken using dermatomed human female abdominal skin (500 μm). These experiments were performed over 24 hours using stainless steel, flow through diffusion cells based on those described previously (Cooper, E. R. J. Pharm. Sci. 1984, 73, 1153-1156) except that the cell was modified to increase the diffusion area to 1.0 cm2. The formulations were applied using a finite dose technique (Franz, T. J. Curr. Probl. Dermatol., 1978, 7, 58-68) to mimic clinical dosing conditions at an applied dose volume of 15 μL/cm2. A piece of stainless steel wire mesh was placed directly below the skin in the receptor chamber of the of the diffusion cell to maintain a turbulent flow of receptor solution below the skin. The diffusion cells were maintained at a flow rate of approximately 1.0 mL/hr by a microcassette peristaltic pump (Watson Marlow 505S UK). The cells were kept at 32±0.5° C. by a heater bar and the samples were collected into appropriately sized glass vials for a period of 24 hr. The receptor solutions (0.002% w/v NaN3) maintained sink conditions below the skin.

The formulations consisted of:—
Comp 1: 2% Testosterone (TES), 5% Octyl Salicylate (OS), 2% polyvinyl pyrrolidine (PVP), 30% isopropyl alcohol (IPA) in ethanol (95%)
Comp 2: 2% TES, 5% OS, 2% PVP, 30% IPA, 0.5% polyethylene glycol 200 (PEG200) in ethanol (95%)
Comp 3: 2% TES, 5% OS, 2% PVP, 30% IPA, 1.0% PEG200 in ethanol (95%)
Comp 4: 2% TES, 5% OS, 2% PVP, 30% IPA, 2.5% PEG200 in ethanol (95%)

The amount of active that permeated the skin was quantified using validated HPLC methods The effect on permeation of TES from using the composition as shown in FIG. 6. PEG200 in combination with OS was found to significantly enhance the permeation of Testosterone through human epidermis in vitro.

Example 4

Investigation into the Effect of PEG200 on Cumulative Testosterone Permeation Through Human Skin In Vitro Methods:

Finite-dose in vitro diffusion studies were undertaken using dermatomed human female abdominal skin (500 μm). These experiments were performed over 24 hours using stainless steel, flow through diffusion cells based on those described previously (Cooper, E. R. J. Pharm. Sci. 1984, 73, 1153-1156) except that the cell was modified to increase the diffusion area to 1.0 cm2. The formulations were applied using a finite dose technique (Franz, T. J. Curr. Probl. Dermatol., 1978, 7, 58-68) to mimic clinical dosing conditions at an applied dose volume of 3.6 μL/cm2. A piece of stainless steel wire mesh was placed directly below the skin in the receptor chamber of the of the diffusion cell to maintain a turbulent flow of receptor solution below the skin. The diffusion cells were maintained at a flow rate of approximately 1.0 mL/hr by a microcassette peristaltic pump (Watson Marlow 505S UK). The cells were kept at 32±0.5° C. by a heater bar and the samples were collected into appropriately sized glass vials for a period of 24 hr. The receptor solutions (0.002% w/v NaN3) maintained sink conditions below the skin.

The formulations consisted of:—
Comp 1: 5% Testosterone (TES), 5% Octyl Salicylate (OS) in ethanol (95%)
Comp 2: 5% TES, 5% OS, 1.0% polyethylene glycol 200 (PEG200) in ethanol (95%)
Comp 3: 5% TES, 5% OS, 2.5% PEG200 in ethanol (95%)

The amount of active that permeated the skin was quantified using validated HPLC methods The effect of the combination of PEG200 and OS in Compositions 2 and 3 is compared with a control Composition 1 in FIG. 7. As shown in FIG. 7, PEG200 in combination with OS was found to significantly enhance the permeation of Testosterone through human epidermis in vitro.

Example 5

Ketoprofen Transdermal Spray: Investigation into the Effect of PEG200 and PEG 400 on Ketoprofen Permeation Through Human Skin In Vitro Methods:

Finite-dose in vitro diffusion studies were undertaken dermatomed skin (Padgett Model B or S electric dermatome set at 500 μm) prepared from excised female, abdominal skin.

These experiments were conducted over 24 hours using flow-through systems with a 1-cm2 administration area. A piece of stainless steel wire mesh was placed directly below the skin in the receptor chamber of the of the diffusion cell to maintain a turbulent flow of receptor solution below the skin. The diffusion cells were maintained at a flow rate of approximately 0.5 mL/hr by a peristaltic pump (Watson Marlow 520S Peristaltic Pump with 313A adaptor and 308MC 8 roller pump-head; Stauff Corporation, Australia). The cells were kept at 32±0.5° C. by a heater bar and the samples were collected into appropriately sized glass vials for a period of 24 hr.

Following a 2-h equilibration of the skin with the receptor solution (RS) of 0.002% sodium azide (NaN3), the stratum corneum surface was dosed with a volume of 3.6 μL/cm2 (unless otherwise indicated) of a test formulation using a positive displacement pipette. The formulation was spread evenly over the skin area using the pipette tip.

The Ketoprofen Transdermal Spray formulations were as follows: —
5.0% Ketoprofen (KETO) in Isopropyl alcohol (IPA) [no enhancer]
5.0% KETO, 5% Octyl Slaicylate (OS) in IPA [OS]
5.0% KETO, 2.5% Polyethylene glycol 200 (PEG 200) in IPA [PEG 200]
5.0% KETO, 5% OS, 2.5% PEG 200 in IPA [OS+PEG 200]

A commercially available ketoprofen gel (approximately 5 mg/cm2) was used as a control. The commercially available gel was applied using a solid cap to simulate the rubbing action required when using the product. Approximately 7 mg gel was applied to the circular surface of a black polypropylene cylindrical cap (Alltech catalogue #98105, diameter 11 mm). The cap was weighed before the gel was rubbed onto the surface of the skin. The gel was rubbed on for 30 seconds (s) and the cap was left on the skin for a further 1 minute with a 3.5 g weight on top. The cap was then re-weighed to determine the actual amount of gel applied. The actual weights of the commercially available gel were used to adjust the permeation data to the levels that would have been achieved with 5 mg/cm2 of KETO applied.

The amount of active that permeated the skin was quantified using validated HPLC methods.

FIG. 8 compares the permeation of ketoprofen from a commercially available transdermal gel with the above spray formulations containing 5% ketoprofen 0 or 5% OS and 0 or 2.5% PEG200 in isopropyl alcohol.

FIG. 9 compares the transdermal permeation of 2.5% ketoprofen composition where the penetration enhancer is PEG200 or PEG400 and where PEG200 and PEG400 are used in combination with OSAL ($2^{nd}$ and $3^{rd}$ columns).

Results:

PEG200 in combination with OS was found to significantly enhance the permeation of KETO through human epidermis in vitro. PEG 400, either alone or in combination with OS, did not enhance the permeation of KETO.

Example 6

Diclofenac Transdermal Spray: Investigation into the Effect of PEG200 and PEG 400 on Diclofenac Permeation Through Human Skin In Vitro Methods:

Finite-dose in vitro diffusion studies were undertaken dermatomed skin (Padgett Model B or S electric dermatome set at 500 μm) prepared from excised female, abdominal skin.

These experiments were conducted over 24 hours using flow-through systems with a 1-cm$^2$ administration area. A piece of stainless steel wire mesh was placed directly below the skin in the receptor chamber of the of the diffusion cell to maintain a turbulent flow of receptor solution below the skin. The diffusion cells were maintained at a flow rate of approximately 0.5 mL/hr by a peristaltic pump (Watson Marlow 520S Peristaltic Pump with 313A adaptor and 308MC 8 roller pump-head; Stauff Corporation, Australia). The cells were kept at 32±0.5° C. by a heater bar and the samples were collected into appropriately sized glass vials for a period of 24 hr.

Following a 2-h equilibration of the skin with the receptor solution (RS) of phosphate-buffered saline (PBS) pH 7.4, the stratum corneum surface was dosed with a volume of 3.6 μL/cm$^2$ (unless otherwise indicated) of a test formulation using a positive displacement pipette. The formulation was spread evenly over the skin area using the pipette tip.

The Diclofenac Transdermal Spray formulations were as follows: —
0.1-2.0% Diclofenac (DIC) diethylamine in Isopropyl alcohol (IPA) [no enhancer]
0.1-2.0% DIC diethylamine, 5% Octyl Salicylate (OS) in IPA [OS alone]
0.1-2.0% DIC diethylamine, 2.5% Polyethylene glycol 200 (PEG 200) in IPA [PEG 200 alone]
0.1-2.0% DIC diethylamine, 5% OS, 2.5% PEG 200 in IPA [OS+PEG 200]

A commercially available Diclofenac gel (approximately 5 mg/cm2) was used as a control. The commercially available gel was applied using a solid cap to simulate the rubbing action required when using the product. Approximately 7 mg gel was applied to the circular surface of a black polypropylene cylindrical cap (Alltech catalogue #98105, diameter 11 mm). The cap was weighed before the gel was rubbed onto the surface of the skin. The gel was rubbed on for 30 seconds (s) and the cap was left on the skin for a further 1 minute with a 3.5 g weight on top. The cap was then re-weighed to determine the actual amount of gel applied. The actual weights of the commercially available gel were used to adjust the permeation data to the levels that would have been achieved with 5 mg/cm$^2$ of DIC applied.

The amount of active that permeated the skin was quantified using validated HPLC methods.

FIG. 10 compares diclofenac DIC permeation from a commercially available gel with compositions containing 2% DIC diethylamine with each of 0% enhancer, 5% OS, 2.5% PEG 200 and 5% OS plus 2.5% PEG 200 (each in isopropyl amine (IPA)).

FIG. 11 comprises the effect of PEG 400 on enhancement with OS.

Results:

PEG200 in combination with OS was found to significantly enhance the permeation of DIC through human epidermis in vitro. PEG 400, either alone or in combination with OS, was found to decrease the DIC permeation.

Example 7

Estradiol Spray: Investigation into the Effect of PEG200 and PEG 400 on Estradiol Permeation Through Human Skin In Vitro Methods:

Finite-dose in vitro permeation studies were undertaken using dermatomed skin (Padgett Model B or S electric dermatome set at 500 µm) prepared from excised female, abdominal skin.

These experiments were conducted over 24 hours (h) using flow-through systems with a 1-cm2 administration area. A piece of stainless steel wire mesh was placed in the receptor chamber of the of each permeation cell to support the skin and to maintain a turbulent flow of receptor solution below the skin. The receptor solution was maintained at a nominal flow rate of 0.5 mL/h by a peristaltic pump (Watson Marlow 520S Peristaltic Pump with 313A adaptor and 308MC 8 roller pump-head; Stauff Corporation, Australia). The cells were placed on a heater bar to keep the temperature of the skin at 32±1° C.

Following a 2-h equilibration of the skin with the receptor solution (RS; 0.002% sodium azide), the stratum corneum surface was dosed with 3.6 µL/cm$^2$ of an Estradiol Transdermal Spray formulation using a positive displacement pipette. The formulation was spread evenly over the skin area using the pipette tip. Permeation samples were collected into appropriately sized glass vials for a period of 24 h.

The Estradiol transdermal spray formulations contained:—
  Estradiol (E2)+Octyl Salicylate (OS) in Isopropyl Alcohol IPA
  E2+OS+Polyethylene glycol (PEG200) in Isopropyl Alcohol IPA
  E2+OS+Polyethylene glycol 400 (PEG400) in IPA The amount of active that permeated the skin was quantified using validated HPLC methods.

FIG. 12 shows the effect of PEG200 and PEG400 on estradiol permeation.

Results:

PEG200 combined with OS synergistically enhanced the permeation of estradiol through human skin in vitro. PEG400 had no significant effect on the permeation of Estradiol when compared with the control formulation—this was true for formulations containing PEG400 alone and PEG400+OS.

The invention claimed is:

1. A transdermal delivery system comprising a composition comprising
   (a) a physiologically active agent;
   (b) a penetration enhancer comprising a combination of
      (i) a $C_6$ to $C_{12}$ alkyl ester of salicylic acid in an amount from 0.1% to 10% by weight of the composition and
      (ii) a polyethylene glycol having an average molecular weight of no more than 300 in an amount from 0.5% to 20% by weight of the composition wherein the weight ratio of the $C_6$ to $C_{12}$ alkyl ester of salicylic acid to the polyethylene glycol is from 10:1 to 1:10; and
   (c) a volatile solvent selected from the group consisting of $C_2$ to $C_4$ alkanols in an amount from 70% to 95% by weight of the composition.

2. A transdermal delivery system according to claim 1, wherein the ester of salicylic acid is the ethylhexyl ester.

3. A transdermal delivery system according to claim 1, wherein the total water content of the composition is less than 10% by weight of the total composition.

4. A transdermal delivery system according to claim 1, which is non-occlusive.

5. A transdermal delivery system according to claim 1, wherein the physiologically active agent comprises one or more active agents selected from the group consisting of antidepressants and hormones.

6. A transdermal delivery system according to claim 1, wherein the physiologically active agent comprises one or more of mirtazapine and esmirtazapine.

7. A transdermal delivery system according to claim 1, wherein the physiologically active agent comprises one or more active agents selected from the group consisting of androgens, estrogens, selective estrogen receptor modulators, aromatase inhibitors, gonadotropins, progesterone, progestins, selective progesterone receptor modulators, antiprogestogen, antigonadotropins, gonadotropin-releasing hormone receptor agonists, antidiarrhoeals, cardiovascular system agents, antihypertensives, calcium channel blockers, proton pump inhibitors, antiarrhyrthmics, antiangina, beta-adrenergic blocking agents, cardiotonic glycosides, adrenergic stimulants, vasodilators, antimigraine preparations, anticoagulants, haemostatic agents, analgesics, antipyretics, hypnotics, antianxiety, neuroleptic and antipsychotic drugs, antidepressants, CNS stimulants, anti-alzheimer's agents, antiparkinson agents, lipid regulating drugs, anticonvulsants, antiemetics, antinauseants, non-steroidal antiinflammatory agents, antirheumatoid, muscle relaxants, diuretics, antidiuretics, obstetric drugs, prostaglandins, antimicrobials, antituberculosis drugs, antimalarials, antiviral agents, anthelmintics, cytotoxic agents, anorectics, agents used in treatment of hypercalcaemia, antitussives, expectorants, decongestants, bronchospasm relaxants, antihistamines, local anaesthetics, stratum corneum lipids, H2-receptor antagonists, neuromuscular blocking agents, smoking cessation agents, insecticides and other pesticides, dermatological agents, allergens, nutraceutically active compounds, keratolytics, anti-acne agents, anti-psoriasis agents, anti-itch agents, anticholinergic agents, and mixtures thereof.

8. A transdermal delivery system according to claim 7, wherein the physiologically active agent is a contraceptive active agent selected from one or more estrogens and one or more progestins.

9. A transdermal delivery system according to claim 7, wherein the drug delivery system comprises on a weight basis from about 0.1 to about 10% of the physiologically active agent, from about 0.1 to 12% of the penetration enhancer and from about 70 to 95% of ethanol, isopropanol or mixture thereof.

10. A transdermal delivery system according to claim 1, provided in a spray apparatus comprising a container containing the transdermal composition, a spray nozzle, and an actuator capable of delivering a metered dose spray from the container via the spray nozzle.

11. A transdermal delivery system according to claim 1, wherein the physiologically active agent is selected from the group consisting of steroidal hormones, non-steroidal anti-inflammatory drugs, and dopamine-2-agonists.

12. A transdermal delivery system according to claim 1, wherein the physiologically active agent is a non-steroidal anti-inflammatory drug selected from the group consisting of ibuprofen, flurbiprofen, keptoprofen, aclofenac, diclofenac, aloxiprin, aproxen, aspirin, diflunisal, fenoprofen, indomethacin, mefanamic acid, naproxen, phenylbutazone, piroxicam, salicylamide, salicylic acid, sulindac, desoxysulindac, tenoxicam, tramadol and ketorolac.

13. A transdermal delivery system according to claim 1, wherein the physiologically active agent is naproxen.

14. A transdermal delivery system according to claim 1, wherein the physiologically active agent is a dopamine-2 agonist.

15. A transdermal delivery system according to claim 1, wherein the physiologically active agent is an anti-thyroid agent.

16. A transdermal delivery system according to claim 1, wherein the PEG has an average molecular weight of 200.

17. A transdermal delivery system according to claim 1, wherein the PEG has the formula H—[OCH$_2$CH$_2$]$_n$—OH, wherein n is 4.

18. A method of transdermal administration of an active agent to an animal subject comprising application to a dermal surface of the animal of a transdermal system according to claim 1.

19. A method of transdermal administration according to claim 18, wherein the animal subject is selected from the group consisting of:
  (a) an animal subject in need of male hormone replacement therapy and the physiologically active agent comprises testosterone;
  (b) an animal subject in need of androgen replacement therapy for females lacking libido and the physiologically active agent comprises an androgen;
  (c) an animal subject in need of female hormone replacement therapy for postmenopausal women and the physiologically active agent comprises an oestrogen;
  (d) an animal subject in need of male contraception and the physiologically active agent comprises a male contraceptive hormone; and
  (e) an animal subject in need of female contraception and the physiologically active agent comprises a female contraceptive hormone.

* * * * *